United States Patent
Franklin et al.

(10) Patent No.: US 11,076,944 B2
(45) Date of Patent: Aug. 3, 2021

(54) METHODS AND SYSTEMS FOR IRRIGATING AND CAPTURING PARTICULATES DURING HEART PUMP IMPLANTATION

(71) Applicant: TC1 LLC, St. Paul, MN (US)

(72) Inventors: Stephen Franklin, Haverhill, MA (US); Rachel Keen, Medford, MA (US)

(73) Assignee: TC1 LLC, Saint Paul, MN (US)

( * ) Notice: Subject to any disclaimer, the term of this patent is extended or adjusted under 35 U.S.C. 154(b) by 103 days.

(21) Appl. No.: 16/363,871

(22) Filed: Mar. 25, 2019

(65) Prior Publication Data

US 2019/0290418 A1    Sep. 26, 2019

Related U.S. Application Data

(60) Provisional application No. 62/648,165, filed on Mar. 26, 2018.

(51) Int. Cl.
*A61F 2/01* (2006.01)
*A61M 60/857* (2021.01)

(52) U.S. Cl.
CPC .......... *A61F 2/013* (2013.01); *A61M 60/857* (2021.01); *A61F 2/011* (2020.05); *A61F 2002/016* (2013.01); *A61F 2250/001* (2013.01)

(58) Field of Classification Search
CPC ........ A61F 2/01; A61F 2/0103; A61F 2/0105; A61F 2/0108; A61F 2/011; A61F 2/012; A61F 2/013; A61F 2/014; A61F 2002/015; A61F 2002/016; A61F 2002/018; A61F 2250/001; A61M 1/008; A61B 2217/007
See application file for complete search history.

(56) References Cited

U.S. PATENT DOCUMENTS

| | | | |
|---|---|---|---|
| 5,695,471 A | 12/1997 | Wampler |
| 5,888,242 A | 3/1999 | Antaki et al. |
| 5,989,281 A | 11/1999 | Barbut et al. |
| 6,071,093 A | 6/2000 | Hart |

(Continued)

FOREIGN PATENT DOCUMENTS

WO    2017202881 A1    11/2017

*Primary Examiner* — Melanie R Tyson
(74) *Attorney, Agent, or Firm* — Kilpatrick Townsend & Stockton LLP

(57) ABSTRACT

The invention relates generally to methods and systems for irrigating or capturing particulates during heart pump implantation, and more specifically relates to irrigating, capturing, and removing particulates that may be released when coring a patient's heart tissue. In one aspect, a method for capturing particulates during heart pump implantation is provided that includes inserting a removable particulate capture device into a patient's heart prior to a coring procedure upon the patient's heart. The removable particulate capture device includes an expandable basket movable between collapsed and expanded configurations. The method further includes expanding the expandable basket to the expanded configuration from the collapsed configuration when the removable particulate capture device is positioned within the patient's heart to capture the particulates released during the coring procedure. The method includes removing the expandable basket with the captured particulates from the patient's heart through a cored opening.

15 Claims, 14 Drawing Sheets

(56) References Cited

U.S. PATENT DOCUMENTS

| | | |
|---|---|---|
| 6,116,862 A | 9/2000 | Rau et al. |
| 6,186,665 B1 | 2/2001 | Maher et al. |
| 6,234,772 B1 | 5/2001 | Wampler et al. |
| 6,245,088 B1 | 6/2001 | Lowery |
| 6,264,635 B1 | 7/2001 | Wampler et al. |
| 6,688,861 B2 | 2/2004 | Wampler |
| 6,689,150 B1 | 2/2004 | Vantassel et al. |
| 6,991,595 B2 | 1/2006 | Burke et al. |
| 7,699,586 B2 | 4/2010 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 2003/0078592 A1 | 4/2003 | Heilman et al. |
| 2005/0071001 A1 | 3/2005 | Jarvik |
| 2005/0119688 A1* | 6/2005 | Bergheim ............... A61F 2/013 606/200 |
| 2006/0074484 A1 | 4/2006 | Huber |
| 2007/0078293 A1 | 4/2007 | Shambaugh, Jr. et al. |
| 2008/0021394 A1 | 1/2008 | LaRose et al. |
| 2009/0203957 A1 | 8/2009 | LaRose et al. |
| 2012/0046514 A1 | 2/2012 | Bourque |
| 2012/0095281 A1 | 4/2012 | Reichenbach et al. |
| 2012/0271341 A1 | 10/2012 | Hill et al. |
| 2013/0096364 A1 | 4/2013 | Reichenbach et al. |
| 2013/0121821 A1 | 5/2013 | Ozaki et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2015/0273124 A1* | 10/2015 | Callaway ............ A61M 1/1008 623/3.26 |
| 2016/0317288 A1* | 11/2016 | Rogers ................... A61F 2/013 |

\* cited by examiner

METHODS AND SYSTEMS FOR IRRIGATING AND CAPTURING PARTICULATES DURING HEART PUMP IMPLANTATION

CROSS REFERENCE TO RELATED APPLICATIONS

The present application claims the benefit under 35 USC § 119(e) of U.S. Provisional Appln. No. 62/648,165 filed Mar. 26, 2018, the full disclosure of which is incorporated herein by reference in its entirety for all purposes.

BACKGROUND

This application relates generally to methods and systems for irrigating and capturing particulates during heart pump implantation, and more specifically relates to irrigating, capturing, and removing particulates that may be released when coring a patient's heart tissue.

Ventricular assist devices, known as VADs, are implantable heart or blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Typically, a component of the VAD (e.g., a pump inflow conduit) is implanted into a patient's heart. The component may be inserted into the heart through an opening or hole cored through heart tissue. When coring a hole through heart tissue during a heart pump implantation process, particulates may be released into the heart which may lead to an increased risk of stroke. Therefore, it would be desirable to provide improved systems and methods for irrigating, capturing, and removing such particulates during the heart pump implantation process.

BRIEF SUMMARY

The invention relates generally to methods and systems for irrigating or capturing particulates during heart pump implantation, and more specifically relates to irrigating, capturing, and removing particulates that may be released when coring a patient's heart tissue. Such methods and systems may be suitable for use during an implantation process to implant a VAD into a patient. In one aspect, a method for capturing particulates during heart pump implantation is provided that includes inserting a removable particulate capture device into a patient's heart prior to a coring procedure upon the patient's heart. The removable particulate capture device includes an expandable basket movable between collapsed and expanded configurations. The method further includes expanding the expandable basket to the expanded configuration from the collapsed configuration when the removable particulate capture device is positioned within the patient's heart, conducting the coring procedure, and capturing particulates released during and/or after the coring procedure within the expandable basket. The method includes removing the expandable basket with the captured particulates from the patient's heart through a cored opening. In some embodiments, the method includes collapsing the expandable basket to the collapsed configuration from the expanded configuration after the coring procedure and prior to removing the expandable basket from the patient's heart.

In some embodiments, the method includes collapsing the expandable basket to the collapsed configuration from the expanded configuration prior to removing the expandable basket from the patient's heart. The method may include attaching an inflow cannula of a heart pump to the patient's heart after removing the expandable basket. In some embodiments, expanding the expandable basket includes expanding until the expandable basket contacts inner walls of the heart. The method may further include inserting a removable particulate capture device into a ventricle of the patient's heart. The method may include collapsing the expandable basket to the collapsed configuration from the expanded configuration prior to inserting the removable particulate capture device within the patient's heart.

In some embodiments, the coring procedure includes coring a portion of the patient's heart (e.g., apex) after inserting the removable particulate capture device into the patient's heart. The method may include creating an access site through a surface of the patient's heart that the removable particulate capture device is configured to be inserted through into the patient's heart. In some embodiments, the access site is different from a second access site for the coring procedure. In some embodiments, the expandable basket includes a mesh basket. In some embodiments, the expandable basket includes self-expandable structural frame members. The method may include inflating a balloon to expand the expandable basket. In some embodiments, the method includes axially moving an actuator relative to a delivery shaft, the actuator being coupled to structural frame members of the expandable basket and the delivery shaft to expand the expandable basket. The method may include inserting a delivery catheter into the patient's heart to insert the removable particulate capture device. In some embodiments, the delivery catheter is configured to surround at least a portion of the removable particulate capture device. The method may further include inserting a removable tissue irrigating device into the patient's heart configured to irrigate particulates released during and/or after the coring procedure. The method may include sewing a ventricular cuff to the patient's heart prior to or after the coring procedure.

In another aspect of the invention, a method for irrigating particulates during heart pump implantation is provided that includes inserting a removable tissue irrigating device into a patient's heart to irrigate the heart of particulates released from a coring procedure. The removable tissue irrigating device includes a delivery tube and at least one irrigation conduit extending therethrough. The method includes extending the irrigation conduit out of an opening in the delivery tube to a deployed position from a stored position, the irrigation conduit being substantially positioned within the delivery tube when in the stored position and having a distal portion protruding out of the delivery tube when in the deployed position. The method further includes dispersing fluid from the irrigation conduit into the patient's heart and removing the tissue irrigating device from the patient's heart. The method may include removing the particulates released during and/or after the coring procedure or by the dispersed fluid. The method may further include coring an opening in the patient's heart. In some embodiments, the removable tissue is inserted through a cored opening in a portion of the patient's heart. The method may include moving the irrigation conduit to the stored position prior to removing the removable tissue irrigating device from the patient's heart. In some embodiments, the method includes attaching an inflow cannula of a heart pump to the patient's heart after removing the removable tissue irrigating device from the patient's heart. The method may include removing particulates (e.g., released during and/or after the coring procedure or by dispersed fluid) by switching a cardiopulmonary bypass machine coupled to the patient's heart from an on position to an off position such that particulates may be ejected from the patient's heart, suctioning the particulates out of the patient's heart (e.g., with an aspiration catheter), or manually by hand (e.g., with tweezers or other suitable tools).

In some embodiments, the method includes inserting a removable particulate capture device into the patient's heart prior to the coring procedure, the removable particulate capture device configured to capture and remove particulates released during and/or after the coring procedure or by the dispersed fluid. In some embodiments, the removable tissue irrigating device includes a plurality of irrigation conduits and fluid is configured to be dispersed from each of the irrigation conduits when the irrigation conduits are in the deployed positions. The irrigation conduit may include a plurality of holes configured to allow fluid to be dispersed therethrough into the patient's heart. In some embodiments, the irrigation conduit extends in a substantially arcuate manner out of the opening in the delivery tube in the deployed position. The method may further include connecting the irrigation conduit to a fluid source. In some embodiments, the removable tissue irrigating device is inserted into a ventricle of the patient's heart.

In another aspect of the invention, a method for irrigating and capturing particulates during heart pump implantation is provided that includes inserting a removable particulate capture device into a patient's heart prior to a coring procedure upon the patient's heart, the removable particulate capture device movable between collapsed and expanded configurations. The method further includes expanding the removable particulate capture device to the expanded configuration from the collapsed configuration when the removable particulate capture device is positioned within the patient's heart. The method includes inserting a removable tissue irrigating device into a patient's heart to irrigate the heart of particulates released from the coring procedure and dispersing fluid from the tissue irrigating device into the patient's heart. The method includes capturing particulates released during and/or after fluid dispersal or the coring procedure. The method includes removing the particulate capture device with the captured particulates and the tissue irrigation device from the patient's heart through a cored opening in the patient's heart tissue.

In yet another aspect of the invention, a medical system for capturing and removing particulates during heart pump implantation is provided that includes a removable particulate capture device configured to be deployed within a patient's heart prior to a coring procedure upon the patient's heart to capture and remove particulates released during and/or after the coring procedure. The removable particulate capture device includes an expandable basket, wherein the expandable basket is movable between collapsed and expanded configurations. The expandable basket is configured to be in the collapsed configuration during delivery into the patient's heart and the expanded configuration when deployed within the patient's heart to capture particulates released during and/or after the coring procedure upon the patient's heart. In some embodiments, the removable particulate capture device is configured to be deployed within a ventricle of the patient's heart. In some embodiments, the expandable basket is configured to contact inner walls of the left ventricle of the patient's heart when in the expanded configuration to secure the expandable basket in position within the patient's heart.

In some embodiments, the medical system includes a delivery system that includes a delivery shaft having a proximal end portion and a distal end portion. The distal end portion is coupled to the expandable basket. The delivery shaft may include a sharpened distal tip extending distally from the distal end portion coupled to the expandable basket. In some embodiments, the delivery shaft includes a guidewire. The delivery system may include an outer shaft extending around at least a portion of the delivery shaft. In some embodiments, the delivery shaft and the expandable basket are axially movable relative to the outer shaft. In other embodiments, the outer shaft is axially movable relative to the delivery shaft and the expandable basket. In some embodiments, the delivery system is integrated with a surgical coring tool.

In certain embodiments, the medical system includes a removable tissue irrigating device configured to irrigate the patient's heart of particulates released during and/or after the coring procedure. In some embodiments, the expandable basket is configured to self-expand from the collapsed configuration to the expanded configuration when deployed within the patient's heart. The expandable basket may include a plurality of structural frame members having proximal and distal ends, wherein the distal ends are coupled to a delivery shaft. In some embodiments, the plurality of structural frame members are elastically deformable. The plurality of structural frame members may be constructed from a shape-memory material.

In some embodiments, the medical system includes an actuator configured to move the expandable basket from the collapsed configuration to the expanded configuration. The actuator may include an inflatable balloon configured to move the expandable basket to the expanded configuration when inflated and to the collapsed configuration when deflated. In some embodiments, the medical system includes a plurality of support members having proximal and distal ends, wherein the proximal ends of the support members are coupled to the actuator and the distal ends of the support members are coupled to the structural frame members, and wherein the actuator is axially movable relative to the delivery shaft to move the expandable basket between the collapsed configuration and the expanded configuration.

In yet another aspect of the invention, a medical system for irrigating particulates during heart pump implantation is provided that includes a removable tissue irrigating device configured to be deployed within a patient's heart to irrigate the heart of particulates released from a coring procedure upon the patient's heart. The removable tissue irrigating device includes a delivery tube and at least one irrigation conduit extending therethrough, the irrigation conduit being movable between stored and deployed positions. The irrigation conduit is configured to be positioned substantially within the delivery tube in the stored position and extend out of an opening in the delivery tube in the deployed position. The irrigation conduit is configured to disperse fluid into the patient's heart when in the deployed position within the patient's heart. The removable tissue irrigating device may be configured to be deployed within the patient's heart after the coring procedure upon the patient's heart. In some embodiments, the removable tissue irrigating device is configured to be deployed within a ventricle of the patient's heart. In some embodiments, the medical system further includes a removable particulate capture device configured to capture particulates released during and/or after the coring procedure. In some embodiments, the removable tissue irrigating device is integrated with a surgical coring tool.

In some embodiments, the medical system further includes a fluid source operably connectable to the irrigation conduit. The fluid source may include at least one of a saline solution filled drip bag or syringe. In some embodiments, the removable tissue irrigating device includes at least three irrigation conduits configured to extend through three separate openings in the delivery tube when each of the irrigation conduits are in the deployed positions. The medical system may include a single fluid source operably connectable to the at least three irrigation conduits. In some embodiments, a distal end portion of the irrigation conduit that protrudes out of the delivery tube through the opening when the irrigation conduit is in the deployed position includes a plurality of holes configured to allow fluid to be dispersed therethrough. A distal end of the irrigation conduit may include a plug, cap, or crimped-tip. In some embodiments, the irrigation conduit extends in a substantially arcuate manner out of the opening in the delivery tube in the deployed position. In certain embodiments, the opening extends through a sidewall of the delivery tube. In some embodiments, the delivery tube includes a blunt distal tip.

In another aspect of the invention, a medical system for irrigating, capturing, and removing particulates during heart pump implantation is provided that includes a removable particulate capture device configured to be deployed within a patient's heart prior to a coring procedure upon the patient's heart to capture and remove particulates released during and/or after the coring procedure, the removable particulate capture device movable between collapsed and expanded configurations. The removable particulate capture device is configured to be moved to the collapsed configuration during delivery into the patient's heart and to the expanded configuration when deployed within the patient's heart to capture particulates released during and/or after the coring procedure upon the patient's heart. The medical system includes a removable tissue irrigating device configured to be deployed within the patient's heart and configured to irrigate the heart of particulates released during and/or after the coring procedure, the removable tissue irrigating device including at least one irrigation conduit configured to disperse fluid into the patient's heart when deployed in the patient's heart. In some embodiments, the removable particulate capture device includes a delivery shaft having a proximal end portion and a distal end portion, wherein the distal end portion is coupled to an expandable basket. The delivery tube may extend around at least a portion of the delivery shaft. In some embodiments, the delivery tube extends coaxially around at least a portion of the delivery shaft. In some embodiments, the delivery shaft is axially movable relative to the delivery tube. In other embodiments, the delivery tube is axially movable relative to the delivery shaft.

In some embodiments, the removable particulate capture device and the removable tissue irrigating device are configured to be deployed within a ventricle of the patient's heart. The removable particulate capture device and the removable tissue irrigating device may be integrated with a surgical coring tool. In some embodiments, the delivery shaft is coupled to the at least one irrigation conduit. The at least one irrigation conduit may be configured to extend out of the delivery tube to disperse fluid into the patient's heart. The delivery tube may include a plurality of inner lumens.

DETAILED DESCRIPTION

Figure 1A:
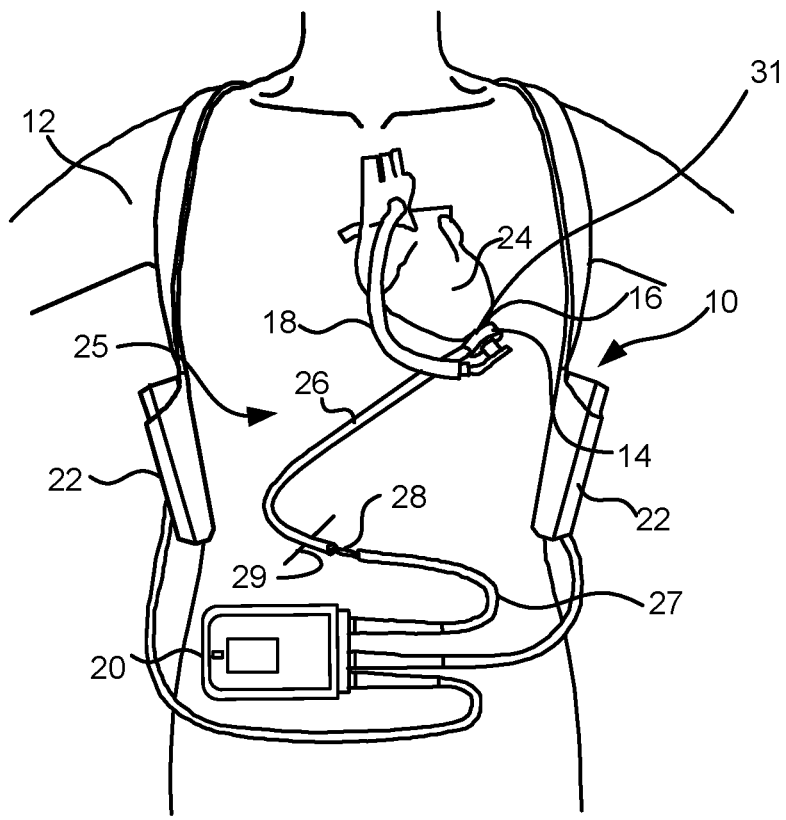
FIG. 1A is an illustration of an implanted mechanical circulatory support system and FIG. 1B is a close-up view of a portion of the implanted mechanical circulatory support system of FIG. 1A in accordance with aspects of the invention.

FIG. 1 is an illustration of a mechanical circulatory support system 10 (e.g., a heart or blood pump system) implanted in a patient's body 12. The mechanical circulatory support system 10 comprises an implantable heart or blood pump 14, ventricular cuff 16, outflow cannula 18, system controller 20, and power sources 22. The implantable blood pump 14 may comprise a VAD that is attached to an apex of the left ventricle, as illustrated, or the right ventricle, or two or more VADS attached to both ventricles of the heart 24. The VAD may comprise a centrifugal (as shown) or axial flow pump that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 1, the blood pump 14 may be attached to the heart 24 via the ventricular cuff 16 which is sewn to the heart 24 and coupled to the blood pump 14. One end of the blood pump 14 may include an inflow conduit or cannula 31 configured to extend into the ventricle via a cored opening in the heart. The other end of the blood pump 14 connects to the ascending aorta via the outflow cannula 18 so that the VAD effectively diverts blood from the weakened ventricle and propels it to the aorta for circulation to the rest of the patient's vascular system.

Figure 1B:
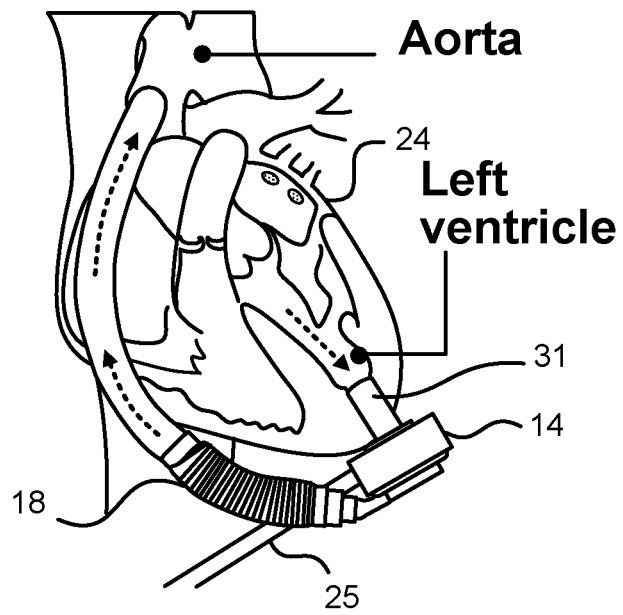
Figure 2A:
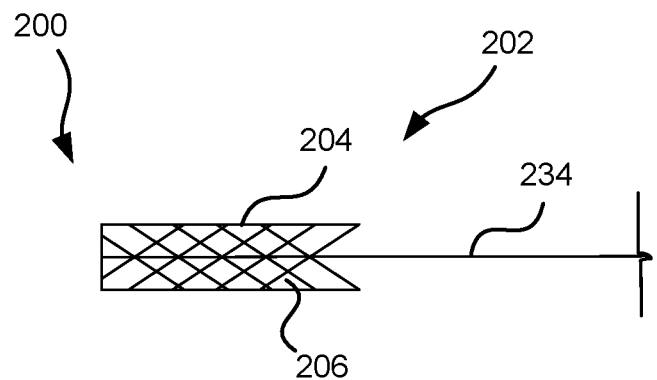
FIGS. 2A and 2B are illustrations of a removable particulate capture device in the collapsed and expanded configurations, respectively, in accordance with aspects of the invention.
Figure 2B:
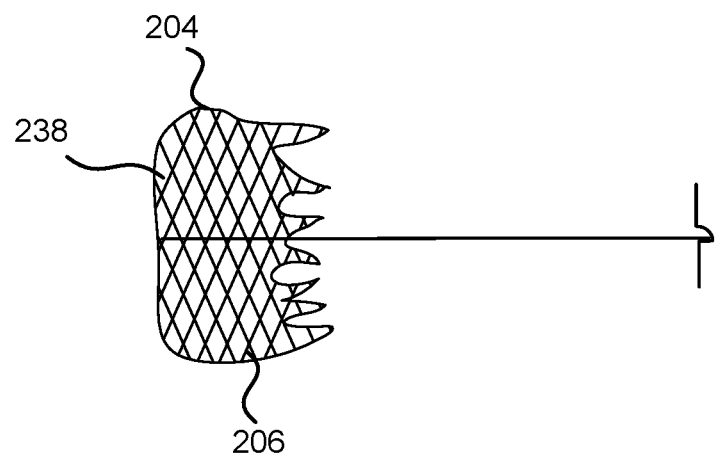

FIGS. 1A-1B illustrate the mechanical circulatory support system 10 during battery 22 powered operation. A driveline cable 25 (e.g., a percutaneous cable or lead) connects the implanted blood pump 14 to the system controller 20, which monitors system 10 operation. The driveline cable 25 may include a percutaneous portion 26 that exits the patient through an exit site 29 (e.g., abdominal aperture) and terminates at in-line connector 28 that connects the percutaneous portion 26 with a modular external cable 27, the other end of the modular external cable 24 being protected within the system controller 20.

The system controller 20 monitors system operations. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22 or other suitable power sources.

With reference to the embodiments illustrated in FIGS. 2A-6E, a medical system 200 for capturing and removing particulates or other thrombi during heart pump implantation (e.g., of the mechanical circulatory support system 10) may include a removable particulate capture device 202 configured to be temporarily deployed within a patient's heart. For example, the capture device 202 may be deployed within a left or right ventricle of a patient prior to a coring procedure. Typically, during heart pump implantation, an opening may be cored through a patient's heart tissue (e.g., myocardium; FIG. 6C). An inflow cannula of a heart pump (e.g., inflow cannula 31) may then be inserted through the cored opening into the ventricle. The capture device 202 may be configured to capture particulates released during such a coring procedure. The capture device 202 may then be withdrawn or removed to remove the particulates after the coring procedure or prior to insertion of the inflow cannula into the ventricle.

The capture device 202 may include an expandable basket 204. For example, the expandable basket 204 may be constructed out of nitinol or other suitable material. In some embodiments, the basket 204 may be a mesh basket (e.g., constructed from a wire mesh, woven material, sheet with laser-cut holes). The expandable basket 204 is movable between collapsed (FIG. 2A) and expanded (FIG. 2B) configurations. For example, the expandable basket 204 may be moved to the collapsed configuration during delivery into or removal from the patient's heart. The expandable basket 204 may be smaller or contracted longitudinally or radially in the collapsed configuration relative to the expanded configuration. In some embodiments, the expandable basket 204 is smaller radially but larger longitudinally (e.g., longer) in the collapsed configuration relative to the expanded configuration. The expandable basket 204 may be moved to the expanded configuration when deployed within the patient's heart to capture particulates released during or throughout the coring procedure. After the coring procedure is completed (e.g., the core has been removed) or prior to implantation of the inflow cannula, the expandable basket 204 may be moved or returned to the collapsed configuration for removal from the patient (e.g., to remove the captured particulates). In some embodiments, the expandable basket 204 may be removed in the expanded configuration from the heart (e.g., through a cored opening in heart tissue). In some embodiments, the expandable basket 204 may include a visual indicator (e.g., light, exposed radiopaque marker, color) to indicated to a clinician that the expandable basket 204 is in the expanded configuration and ready to capture particulates.

In some embodiments, the expandable basket 204 includes a plurality of elastically deformable (e.g., nitinol) structural frame members 206 (e.g., struts, links) configured to allow the expandable basket 204 to move between the collapsed and expanded configurations. In some embodiments, the expandable basket 204 may be configured to self-expand from the collapsed configuration to the expanded configuration when deployed within the patient's heart. In some embodiments, the structural frame members 206 may be constructed from a shape-memory material. When inserted into the patient's heart, the structural frame members 206 may move the expandable basket 204 to the expanded configuration as the structural frame members 206 are exposed to a higher temperature (e.g., internal temperature of the patient). In other embodiments, shape-memory structural frame members 206 may be configured to self-expand to move the expandable basket 204 from the collapsed configuration to the expanded configuration. For example, as described in more detail below, the expandable basket 204 may be delivered via a delivery tube or outer sheath in a collapsed configuration and move to the expandable configuration when released from the outer sheath (e.g., remove a force maintaining the basket 204 in the collapsed configuration during delivery). The basket 204 may also be moved or returned to the collapsed configuration from the expanded configuration as described in more detail below. In some embodiments, the expandable basket 204 is configured to expand until the structural frame members 206 push against inner walls of the patient's heart (e.g., ventricle) to secure the expandable basket 204 in position within the patient's heart in the expanded configuration. In some embodiments, the expandable basket 204 excludes any additional anchors as the expandable basket 204 is configured to be removable as discussed above. However, in other embodiments, the expandable basket 204 may include additional anchors configured to temporarily secure the expandable basket 204 in position within the patient's heart until it is ready to be removed.

Figure 3A:
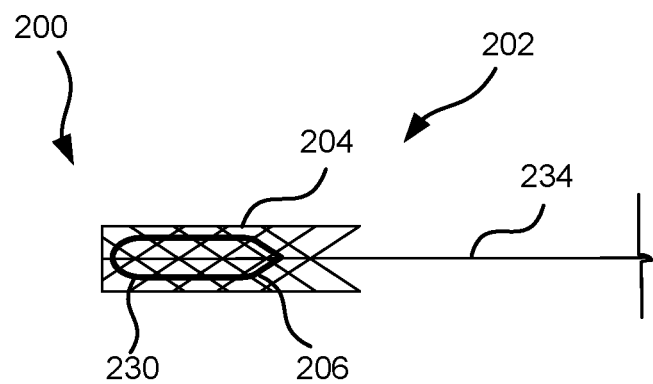
FIGS. 3A and 3B are illustrations of a removable particulate capture device in the collapsed and expanded configurations, respectively, with an inflatable balloon actuator in accordance with aspects of the invention.
Figure 3B:
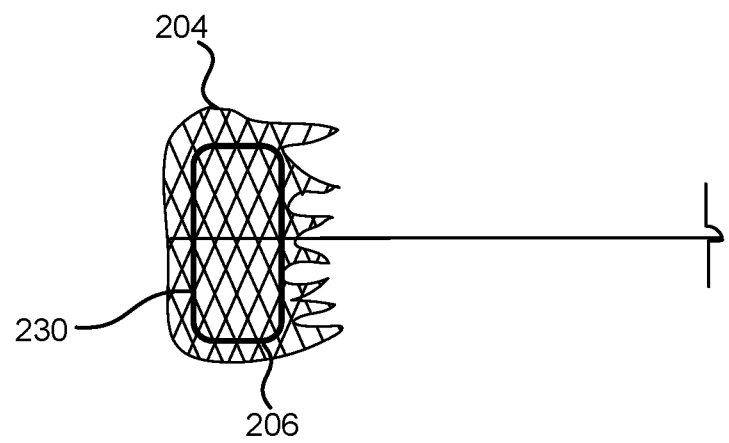

In some embodiments, the capture device 202 includes a deployment mechanism configured to move the expandable basket 204 between collapsed and expanded configurations. For example, the capture device 202 may include an actuator. With reference to FIGS. 3A-3B, in some embodiments, the actuator includes an inflatable balloon 230 operably coupled to or integrated with the expandable basket 204. The inflatable balloon 230 is configured to move the expandable basket 204 to the expanded configuration when inflated. In some embodiments, the inflatable balloon may move the expandable basket 204 to the collapsed configuration when deflated. In some embodiments, the expandable basket 204 is configured to move to the expanded configuration when the balloon is inflated and remain in the expanded configuration after the balloon is deflated. The balloon 230 may extend longitudinally along the expandable basket or delivery shaft as illustrated in FIG. 3A. In other embodiments, the balloon 230 may extend around the expandable basket circumferentially (e.g., along an inner diameter of the expandable basket).

Figure 4A:
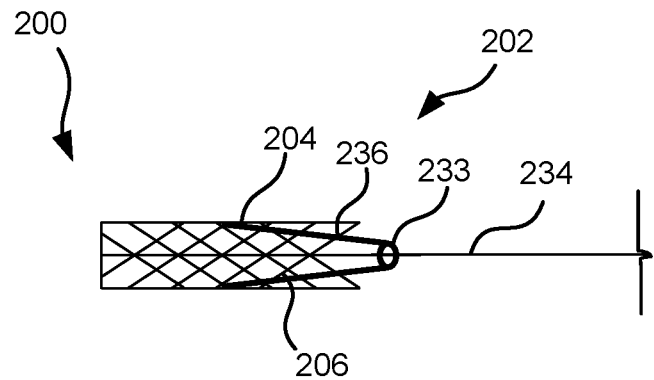
FIGS. 4A and 4B are illustrations of a removable particulate capture device in the collapsed and expanded configurations, respectively, with a hub actuator in accordance with aspects of the invention.
Figure 4B:
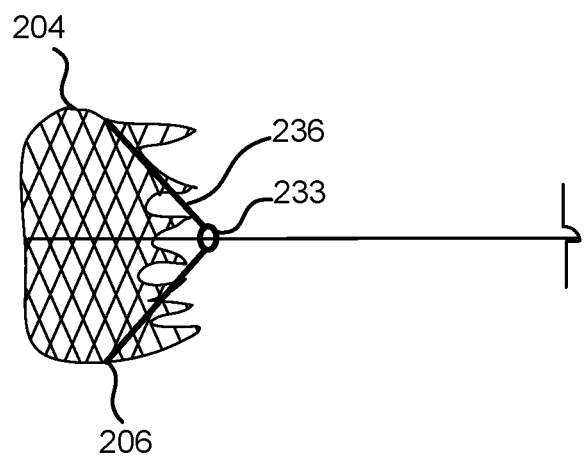

With reference to FIGS. 4A-4B, in other embodiments, the actuator may include a movable (e.g., axially slidable) runner or hub 233. The hub 233 may be coupled to a delivery shaft 234 (e.g., as described in more detail below with respect to delivery mechanism 232 and FIGS. 5A-5B). The delivery shaft 234 may be coupled to the expandable basket 204. The capture device 202 may include a plurality of support ribs or members 236 (e.g., extenders or stretcher) configured to expand or collapse the structural frame members 206 of the expandable basket 234. First ends (e.g., proximal ends) of the support members 236 may be coupled to the hub 233. Second ends (e.g., distal ends) of the support members 236 may be coupled to the structural frame members 206. The hub 233 may be movable in a first direction (e.g., proximally) along the delivery shaft 234 to pull the structural frame members 206 radially inward via the support members 236 (e.g., to collapse the expandable basket 204). The hub 233 may be movable in a second direction (e.g., distally) along the delivery shaft 234 to push the structural frame members 206 radially outward (e.g., to expand the expandable basket 204).

As described above, the expandable basket 204 may be moved to the expanded configuration to capture particulates released during a heart coring procedure. Openings between the structural frame members 206 may be sized to capture such particulates (e.g., the particulates having a size of about 200 µm or smaller, about 150 µm or smaller, about 100 µm or smaller, about 50 µm or smaller, about 10 µm or smaller, about 5 µm or smaller, about 2 µm or smaller, between about 2 µm to about 200 µm, between about 2 µm to about 150 µm, between about 2 µm to about 100 µm, between about 2 µm to about 50 µm, between about 2 µm to about 10 µm, between about 2 µm to about 5 µm, or any value therebetween). The expandable basket 204 may also include a mesh membrane, liner, or cover layer 238 (e.g., a polymer mesh) over at least a portion of the structural frame members 206 to capture the particulates. In such embodiments, openings in the mesh cover layer 238 may be sized to capture such particulates (e.g., about 100 µm or smaller). In some embodiments, the openings between the structural frame members 206 or mesh cover layer 238 are sized such that little to no fluid (e.g., blood) may flow through or past the expandable basket 204 when positioned in the patient's heart. As described in more detail below (FIGS. 6A-6E), during heart pump implantation, the patient may be coupled to a cardiopulmonary bypass machine such that blood bypasses the heart chambers and does need to flow through the expandable basket 204 In other embodiments, the openings between the structural frame members 206 or mesh cover layer 238 are sized such that fluid (e.g., blood) may flow through or past the expandable basket 204 when positioned in the patient's heart (e.g., such that the expandable basket 204 may be removed after a coring procedure with the captured particulates but without also removing a substantial amount of blood from the patient's heart). In some embodiments, when the cardiopulmonary bypass machine is in an off-position as described in more detail below, blood may flow or be pumped out the heart to remove such particulates. In such embodiments, the openings may be sized to allow blood or other fluid to flow through the expandable basket 204.

Figure 5A:
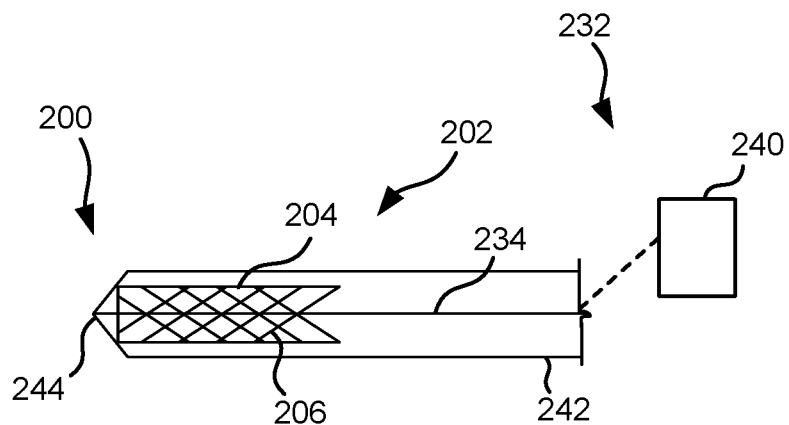
FIGS. 5A and 5B are illustrations of a removable particulate capture device in the collapsed and expanded configurations, respectively, with a delivery mechanism in accordance with aspects of the invention.
Figure 5B:
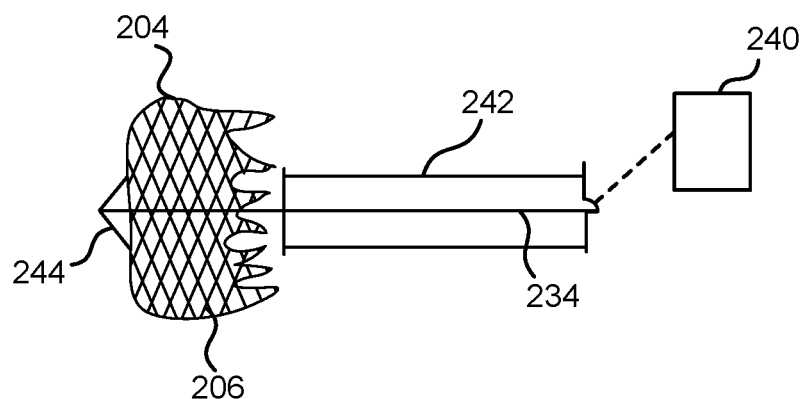

Referring to FIGS. 5A-5B, in some embodiments, the medical system 200 includes a delivery mechanism 232 configured to deliver or insert as well as withdraw or remove the capture device 202. As discussed above, the delivery mechanism may include the delivery shaft 234 (e.g., sheath, catheter, sleeve, lumen, tube, conduit) coupled to the expandable basket 204. In some embodiments, the delivery shaft 234 is configured to be non-detachable from the expandable basket 204 as the expandable basket 204 is configured to be removed after particulates are captured or before the inflow cannula is inserted. However, in other embodiments, the delivery shaft 234 may be configured to be detachable to deploy the expandable basket 204 in the heart to capture particulates and re-attachable to remove the expandable basket 204 once the coring procedure is completed or prior to installation of the inflow cannula. In some embodiments, the delivery mechanism 232 is a catheter-type delivery system. For example, the delivery shaft 234 may include a distal end portion coupled to the expandable basket 204 and a proximal end portion coupled to one or more catheter handles (e.g., a first catheter handle 240) with controls for steering, moving, actuating, locking or rotating associated delivery shafts or conduits). In some embodiments, the delivery mechanism 220 includes one or more guidewires to aid in positioning or inserting the capture device 202 in the patient's heart. The delivery mechanism 220 may include an outer sheath 242 (e.g., shaft, catheter, sleeve, lumen, tube, conduit) or guide catheter coupled to the first catheter handle or to a separate second catheter handle. The outer sheath 242 is configured to extend around at least a portion of the delivery shaft 234. The delivery shaft 234 may be guided or positioned in the patient's heart via or along with the outer sheath 242.

In some embodiments, the delivery shaft 234 is movable relative to the outer sheath 242 (e.g., may be pushed distally out of the outer sheath 242) to deploy the expandable basket 204 out of the outer sheath 242 and into the patient's heart. In other embodiments, the outer sheath 242 is movable relative to the delivery shaft 234 (e.g., may be moved or slid proximally) to deploy the expandable basket 204 out of the outer sheath 242 and into the patient's heart. In some embodiments, the delivery shaft 234 and outer sheath 242 are both movable relative to each other. As described above, the expandable basket 204 may include elastically deformable structural frame members 206 such that it may self-expand (e.g., automatically) to the expanded configuration as it is deployed out of or released from the outer sheath 242. The expandable basket 204 may be stowed or maintained (e.g., constrained) in the collapsed configuration by the outer sheath 242 (e.g., or other intermediary sheaths as described below) until it is deployed or released into the heart.

In some embodiments, the delivery mechanism 232 may include a sharpened distal tip 244. For example, a distal tip of the outer sheath 242 or delivery shaft 234 may be provided with a blade or sharpened edge to cut through heart tissue when inserting the capture device 202 into the heart or make an incision that the capture device 202 may be inserted through into the heart. In other embodiments, the delivery mechanism 220 may include an atraumatic or blunt distal tip. In such embodiments, an access site or incision through the heart tissue of the patient may be created prior to inserting the capture device 202.

In some embodiments, the delivery mechanism 220 includes one or more intermediary or additional shafts or sheaths (e.g., catheters, sleeves, lumens, tubes, conduits, guidewires) between the delivery shaft 234 and the outer sheath 242, within or extending through the delivery shaft, or surrounding at least a portion of the outer sheath 242 (e.g., delivery or guide catheter or sheath). Such intermediary or additional sheaths may be configured to help guide or deploy the expandable basket 204. For example, additional sheaths may be configured as a pusher to push the expandable basket 204 or delivery shaft 234 out of the outer sheath 242, provide pathways for fluids (e.g., for suction or aspiration, inflating a balloon 230 or actuating a hub 233 as described above, or for irrigation as described in more detail below), or for moving an actuator (e.g., hub 233) to expand or collapse the expandable basket 204. While illustrated as extending coaxially or concentrically relative to each other, in other embodiments, the delivery shaft 234, outer sheath 242, or one or more intermediary sheaths may have a non-coaxial or non-concentric configuration. For example, the outer sheath 242 may include a plurality of lumens off-set from a center of the outer sheath 242 and configured to receive the delivery shaft 242 or one or more intermediary sheaths.

FIGS. 6A-6E illustrate a series of views of an exemplary heart pump implantation procedure or process including insertion and removal of the capture device 202. Implantation of the blood pump 14 to the heart 24 may include selecting a location to attach the ventricular cuff 16. For example, an apex 229 of the left ventricle may be selected as an operation site. The ventricular cuff 16 may be positioned in contact with the selected operation site.

Figure 6A:
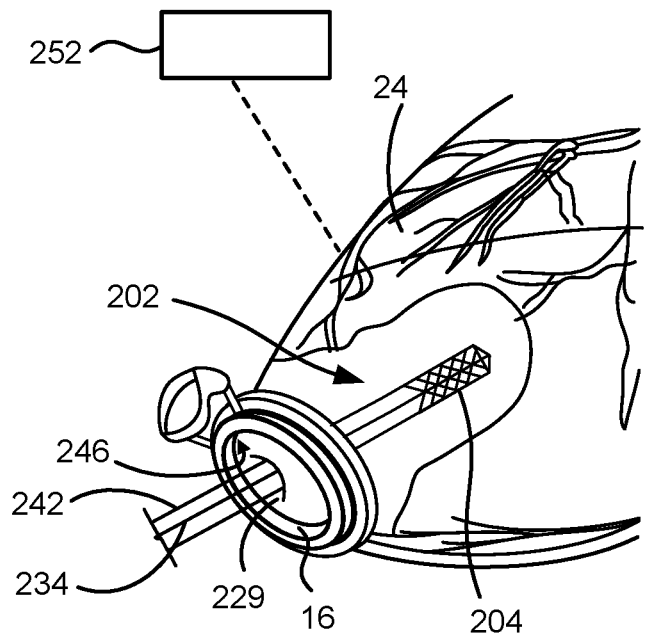
FIGS. 6A-6E are a series of views illustrating an exemplary heart pump implantation procedure or process including insertion and removal of the removable particulate capture device in accordance with aspects of the invention.
Figure 6B:
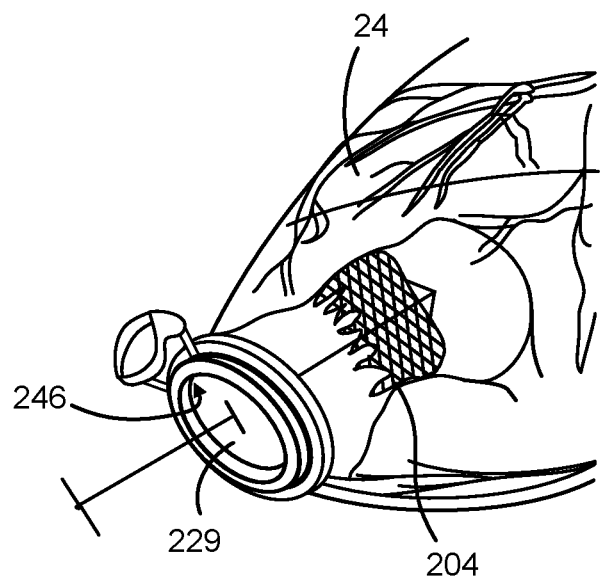

As illustrated in FIG. 6A, the ventricular cuff 16 may then be sewn or otherwise attached to the heart 24. The capture device 202 may then be inserted into the heart 24 through an opening 246 defined by the ventricular cuff 16 configured to receive the inflow cannula 31 of the blood pump 14. As described above the delivery shaft 234 or outer sheath 242 may include a sharpened distal tip 244 configured to puncture the heart tissue such that the expandable basket 204 may be inserted into the heart 24. In other embodiments, an access site or incision may be made through the heart tissue by a separate tool prior to inserting the capture device 202. For example, the access site may be a site created for coring the heart or another separate access site. In some embodiments, the expandable basket 204 may be inserted or otherwise delivered into the heart 24 in the collapsed configuration via the delivery mechanism 232. Once the expandable basket 204 is in a desired position (e.g., in the left ventricle), the expandable basket 204 may be moved to the expanded configuration (FIG. 6B). As described above, the expandable basket 204 may self-expand as it is deployed or released from the outer sheath 242 or include an actuator to move the expandable basket 204 to the expanded configuration. The outer sheath 242 may then be removed from the patient if the delivery mechanism 220 includes an outer sheath.

Figure 6C:
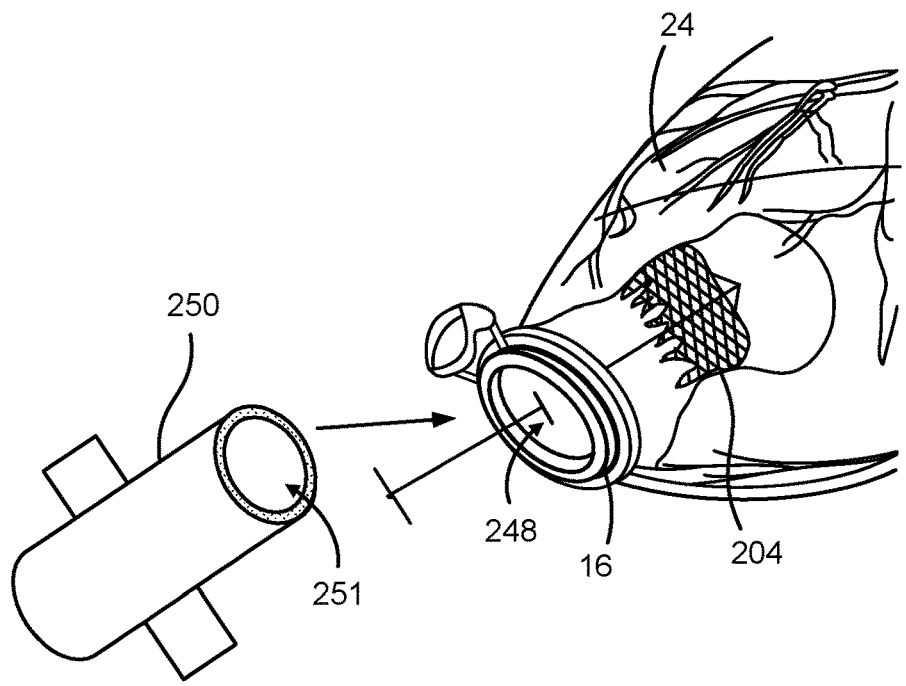
Figure 6D:
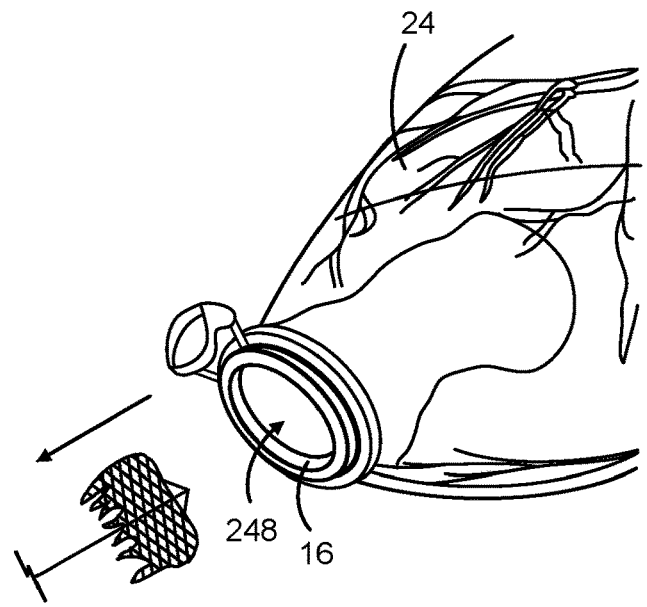
Figure 6E:
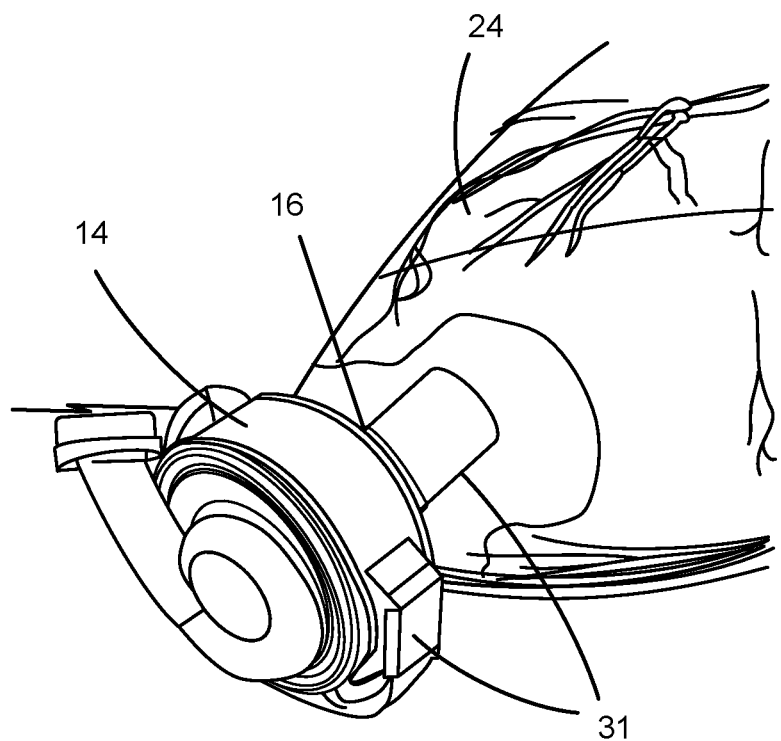
Figure 7A:
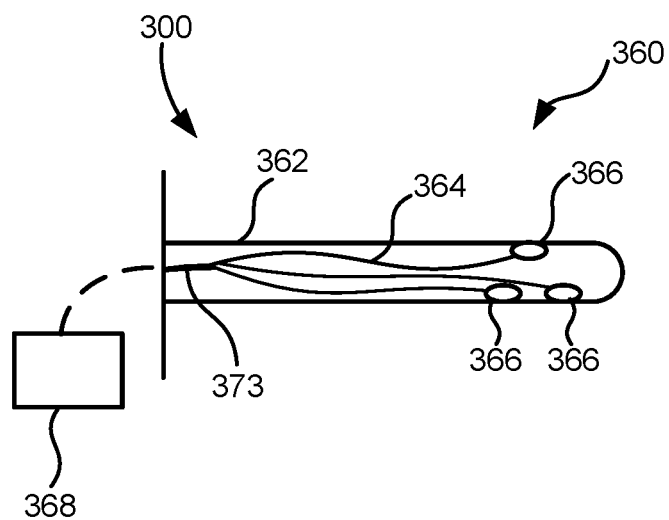
FIGS. 7A and 7B are illustrations of a tissue irrigating device in the stored and deployed configurations, respectively, in accordance with aspects of the invention.
Figure 7B:
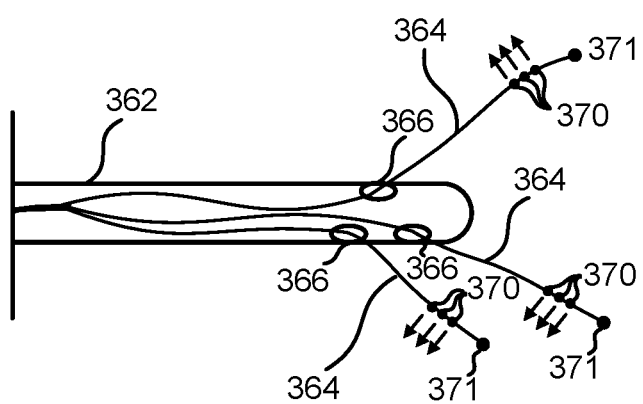

With reference to FIG. 6C, an opening or hole 248 in the heart tissue may then be formed by a coring procedure performed upon the portion of the heart defined by the opening 246 in the ventricular cuff 16. For example, a clinician may use a surgical coring tool 250 (e.g., a coring knife) or other suitable knife to core or remove the portion of the heart (e.g., heart tissue at apex 229 including myocardium) of FIG. 6B. During the coring procedure, the expandable basket 204 is configured to capture released particulates. In the expanded configuration, the expandable basket 204 includes a cavity or concave opening oriented or facing the cored opening or opening to be cored to capture the released particulates. After the coring procedure is completed (e.g., the core has been removed) or prior to installation or attachment of the blood pump 14 to the heart via the ventricular cuff 16, the expandable basket 204 may be removed or withdrawn from the heart (FIG. 6D). In some embodiments, the expandable basket 204 is moved to the collapsed configuration from the expanded configuration and then withdrawn to remove the captured particulates. In other embodiments, the expandable basket 204 is withdrawn or removed with the captured particulates directly in the expanded configuration. In some embodiments, if the delivery shaft 234 is detachable from the expandable basket 204, the delivery shaft 234 is detached after the expandable basket 204 is deployed to capture particulates and re-attached for removal of the expandable basket 204 after the coring procedure is completed. In some embodiments, in addition to, or alternatively, particulates may be removed manually by a clinician (e.g., with tweezers), by suction (e.g., via an aspiration conduit), or deactivating a cardiopulmonary bypass machine as described in more detail below.

After the expandable basket 204 is removed, the inflow cannula 31 of the blood pump 14 may be inserted into heart opening 248 through the ventricular cuff 16 and the blood pump 14 may be coupled to the ventricular cuff 16. Generally, during the implantation process, the ventricular cuff 16 will be first attached to the heart 24 and then heart tissue will be removed or cored (e.g., core section of heart tissue removed through the cuff 16) to insert the inflow cannula 31 as described above. However, in other embodiments, in addition to, or alternatively, heart tissue may also be removed or cored prior to attaching the ventricular cuff 16 to the heart 24. In such embodiments, the capture device 202 may be inserted or removed prior to attaching the ventricular cuff 16. For example, the expandable basket 204 may be inserted into the heart prior to a coring procedure. The cuff 16 may then be attached after the coring procedure. The basket 204 may be removed prior to or after attaching the cuff 16. Related ventricular cuffs and attachment and coring procedures applicable to the present invention are described in U.S. Patent Publication Nos. 2015/0273124, which is incorporated herein by reference for all purposes in its entirety.

With reference to FIGS. 6A-6E together, in some embodiments, the patient (e.g., veins and arteries near the heart 24) may be coupled to a cardiopulmonary bypass machine 252 during at least a portion of the heart pump implantation process. The bypass machine 252 may be activated (e.g., in an on position) such that blood bypasses the heart chambers and does not circulate through the heart or deactivated (e.g., in an off position) such that blood circulates through the heart as necessary during the implantation process. Generally, the bypass machine 252 is activated until the heart pump implantation process is complete. However, the bypass machine may be deactivated at times (e.g., temporarily or periodically) to allow blood to circulate through the heart as necessary. Alternatively, in other embodiments, the heart pump implantation process may be completed (e.g., the ventricular cuff 16 can be coupled to the heart 24 and heart tissue cored and removed) in the absence of a bypass machine 252.

As described above, the surgical coring tool 250 (e.g., a coring knife) may be used to core a portion of the heart during heart pump implantation. In some embodiments, the delivery mechanism 220 or capture device 202 is integrated with the surgical coring tool 250. For example, a body or shaft of the surgical coring tool 250 may include a lumen 251. The delivery mechanism 220 or capture device 202 (e.g., delivery shaft 234 or expandable basket 204) may be configured to extend through such a lumen to be deployed into the patient's heart prior to coring by the surgical coring tool 250. In yet, further embodiments, as described in more detail below with reference to FIG. 9, the capture device 202 or delivery mechanism 220 may be integrated with a tissue irrigating device as described herein.

With reference to the embodiments illustrated in FIGS. 7A-8C, a medical system 300 for irrigating or rinsing away particulates or other thrombi during heart pump implantation (e.g., of the mechanical circulatory support system 10) may include a removable irrigation device 360 configured to be temporarily deployed within a patient's heart. The irrigation device 360 may be deployed within a left or right ventricle of a patient after a coring procedure to irrigate the cored opening or ventricle after the core has been removed. The irrigation device 360 may then be withdrawn or removed prior to implantation of the blood pump (e.g., insertion of the inflow cannula into the ventricle). In other embodiments, the irrigation device 360 may be deployed within the cored opening or section of the heart (e.g., within the cored opening in the myocardium), a ventricle, or both the cored opening and ventricle. In other embodiments, in addition to, or alternatively, the irrigation device 360 may be deployed or positioned proximate to, over, or outside a cored opening of the heart to irrigate, flush, or rinse away particulates (e.g., near an edge or periphery of the cored opening).

The irrigation device 360 includes a delivery tube 362 (e.g., catheter, sleeve, lumen, tube, conduit) and one or more irrigation conduits 364 (e.g., 2, 3, 4, 5) extending therethrough. The irrigation conduits 364 may be movable between stowed or stored positions and deployed positions. In the stored positions (FIG. 7A), the irrigation conduits 364 are positioned substantially within the delivery tube 362. In the deployed positions (FIG. 7B), the irrigation conduits 364 are configured to extend or protrude out of openings 366 in the delivery tube 362. The irrigation conduits 364 are configured to disperse fluid into a cored opening or other portion of the heart (e.g., ventricle) for irrigating or rinsing away particulates when in the deployed positions within the patient's heart. The irrigation conduits 364 may be moved to the stored or stowed positions for delivery or removal (e.g., in a more compact configuration). In some embodiments, the irrigation conduits 364 may be directly inserted into the patient's heart to disperse fluid (e.g., without a delivery tube). For example, one or more irrigation conduits may be disposed or positioned directly in a portion of the patient's heart to irrigate particulates. In some embodiments, the delivery tube 362 functions as the irrigation conduit without additional conduits 364 extending therethrough (e.g., openings to disperse fluid as described in more detail below are disposed on the delivery tube 362). In some embodiments, the irrigation conduits 364 are entirely stowed within the delivery tube 362 when in the stored position.

In some embodiments, the irrigation device 360 includes a fluid source 368 operably connectable or coupleable to the irrigation conduits 364 to deliver irrigating fluid. For example, the irrigation conduits 364 may be coupled to a saline solution filled drip bag, syringe, pump or other suitable fluid source. In some embodiments, each of the irrigation conduits 364 are coupled to a single fluid source 368. For example, proximal ends of the irrigation conduits 364 may be coupled to or funneled into a single conduit in fluid communication with the fluid source 368. In other embodiments, the irrigation conduits 364 are coupled to two or more or separate fluid sources. Distal end portions of the irrigation conduits 364 configured to protrude out of the delivery tube 362 through the openings 366 when in the deployed position may include a plurality of holes 370. In some embodiments, the irrigation conduits 364 may include two or more, three or more, four or more, or five or more openings 366. Fluid (e.g., from fluid source 368) may flow or spray out of the holes 370 to irrigate the patient's heart. In some embodiments, distal tips or ends of the irrigation conduits 364 include plugs 371, are crimped, or are otherwise closed-ended. By closing ends of the irrigation conduits 364, increased fluid pressure may be directed out of the holes 370. In some embodiments, the irrigation conduits 364 are configured to be flexible or bendable (e.g., elastically deformable) or include atraumatic tips such as to prevent or reduce a likelihood of damage to or catching on portions of the heart as the irrigation conduits 364 are moved between the stored and deployed positions and/or when the irrigation device 360 is inserted or withdrawn. In some embodiments, distal portions of the irrigation conduits 364 (e.g., portions configured to protrude out of the delivery tube 362 and into the heart) may be more flexible relative to proximal portions.

As illustrated, the openings 366 in the delivery tube 362 that the irrigation conduits 364 are configured to extend out of in the deployed positions may be spaced apart from a distal tip or end of the delivery tube. For example, the openings 366 may be located or extend through sidewalls (e.g., outer side surfaces) of the delivery tube 362. In other embodiments, the irrigation conduits 364 may extend out of one or more openings 366 at a distal tip or end of the delivery tube 362 in the deployed positions. While illustrated as extending in a substantially arcuate manner out of the openings 366, in other embodiments, the irrigation conduits 364 may extend in a substantially non-arcuate manner out of the openings 366 in the delivery tube (e.g., at oblique or non-oblique angles). In some embodiments, the irrigation conduits 364 extend out of the openings 366 at a suitable angle to irrigate the particulates (e.g., between about 90 degrees to about 120 degrees, between about 120 degrees to about 150 degrees, between about 150 degrees to about 180 degrees, or any value therebetween). In some embodiments, the delivery tube 362 includes an atraumatic or blunt distal tip as the irrigation device 360 may be configured to be positioned in the heart through a cored opening. Such an atraumatic tip may also prevent or reduce a likelihood of damage to the heart as the delivery tube 362 is inserted or removed as described in more detail below.

Figure 8A:
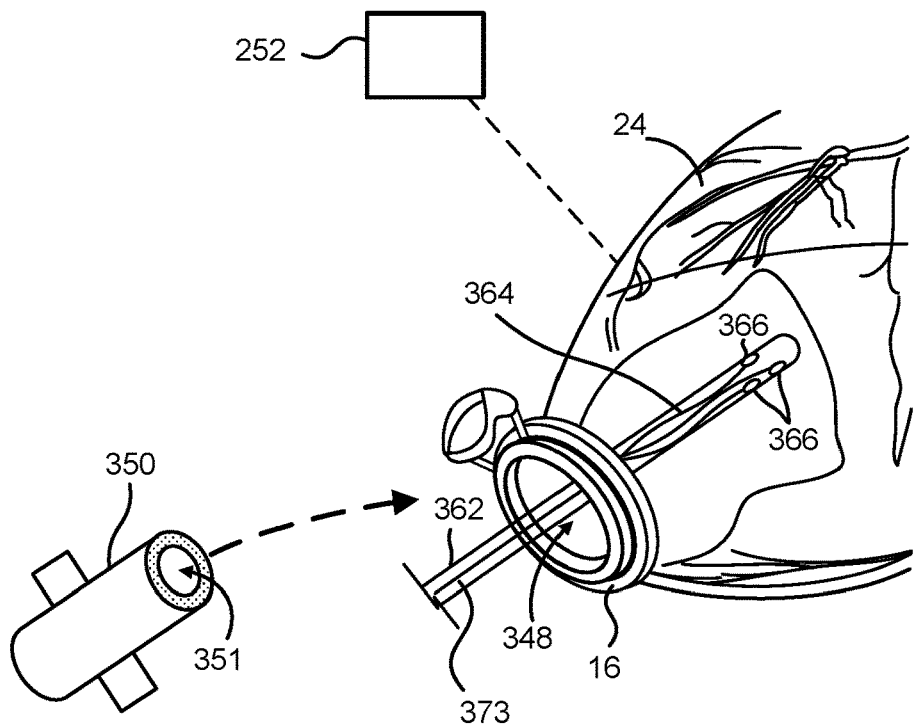
FIGS. 8A-8C are a series of views illustrating an exemplary heart pump implantation procedure or process including insertion and removal of a tissue irrigating device in accordance with aspects of the invention.
Figure 8B:
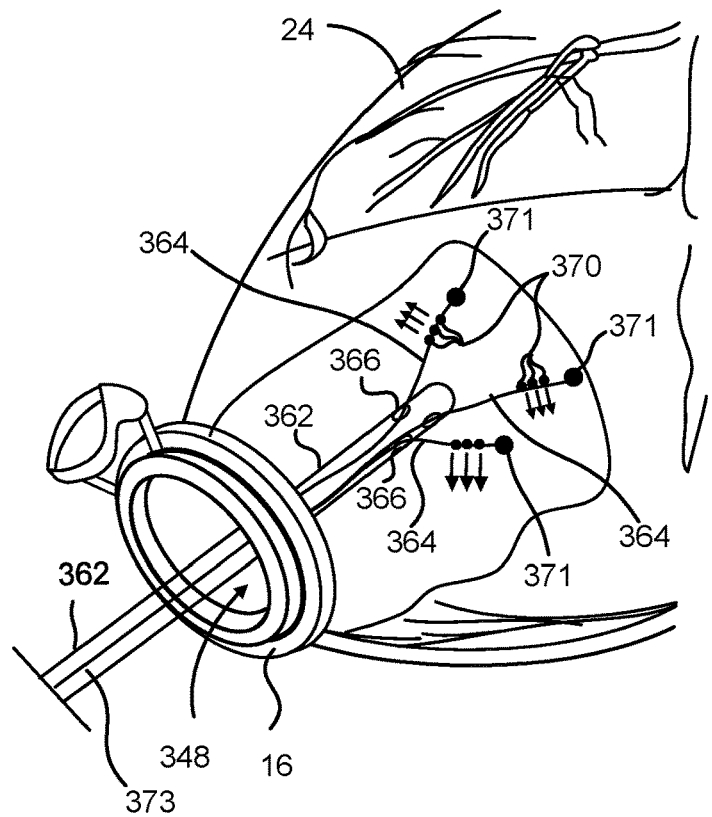
Figure 8C:
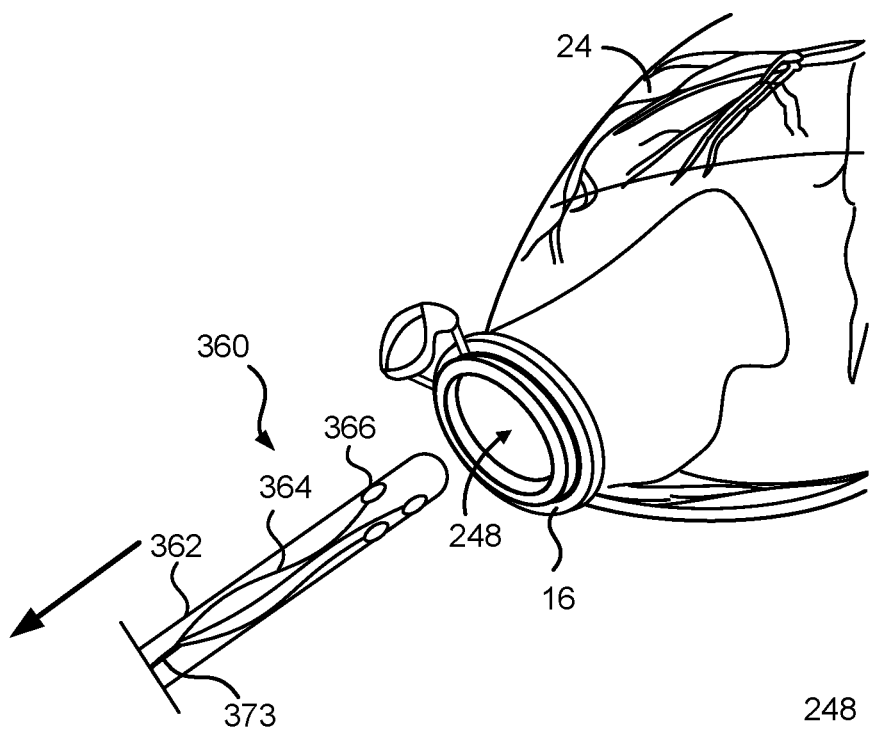

FIGS. 8A-8C illustrate a series of views of an exemplary heart pump implantation procedure or process including insertion and removal of the irrigation device 360. The heart pump implantation procedure may include one or more of any of the steps described above and illustrated in FIGS. 6A-6E (e.g., selecting an operation site, attaching the ventricular cuff 16, inserting or removing a capture device, coring a portion of the heart). As illustrated in FIG. 8A, after a coring procedure has been completed with a surgical coring tool 350 and cored heart tissue removed, the irrigation device 360 may be delivered or inserted into the heart (e.g., ventricle, cored opening in myocardium, or both) through the cored opening 348 in the stored position. In some embodiments, the irrigation device 360 may be inserted through an opening defined by the ventricular cuff 16 through the cored opening when the ventricular cuff 16 is attached to the heart prior to the coring procedure. In other embodiments, the irrigation device 360 may be inserted prior to a coring procedure. For example, in some embodiments, the irrigation device 360 is integrated with the surgical coring 350 tool, the capture device 202, or both the surgical coring tool 350 and the capture device 202 as described in more detail below.

As illustrated in FIG. 8B, when the irrigation device 360 is in position within the heart 24 (e.g., cored opening, ventricle, or both), the irrigation conduits 364 may be moved to the deployed positions and extend out of openings 366 in the delivery tube 362. The proximal ends of the irrigation conduits 364 or delivery tube 362 may be operatively coupled to one or more catheter handles 240 with controls for extending and retracting the delivery tube 362 or irrigation conduits 364. In some embodiments, a pusher shaft 373 (e.g., a delivery shaft) may extend through a proximal end portion of the delivery tube 362 configured to move the irrigation conduits 364 between the stored and deployed positions. In some embodiments, the pusher shaft is coupled to the irrigation conduits 364 such that they can be extended or retracted simultaneously from the delivery tube 362 (e.g., by moving the pusher shaft axially in a distal or proximal within the delivery tube 362). In other embodiments, the irrigation conduits 364 may be moved between the stored and deployed positions independently or separately from each other. In such embodiments, each of the conduits 364 may be coupled to separate pusher shafts. In other embodiments, each of the conduits 364 may be coupled to the catheter handle or moved directly. In some embodiments, the conduits 364 may taper or funnel into a single conduit or shaft (e.g., at a proximal end). In the deployed positions, the irrigation conduits 364 are configured to disperse fluid from the fluid source 368 into the patient's heart to irrigate the heart (e.g., ventricle walls, heart, cored opening walls).

As discussed above with respect to FIGS. 6A-6E, a patient may be coupled to a cardiopulmonary bypass machine during at least a portion of the heart pump implantation process. While the bypass machine is generally activated until the heart pump implantation process is complete, the bypass machine may be deactivated at times (e.g., temporarily or periodically) to allow blood to circulate through the heart. As such, the bypass machine may be deactivated after dispersing fluid with the irrigation device 360 to push or remove particulates out of the heart (e.g., allow blood with any loose particulates to be pumped out of the cored opening). In some embodiments, a clinician may alternate or cycle between dispersing fluid and deactivating the bypass machine multiple times while the irrigation device 360 is deployed within the heart. In yet other embodiments, a delivery tube 362 may include a suction or aspiration lumen or conduit to aspire loose particulates released by irrigating with the irrigation device 360. In some embodiments, the irrigation device 360 may be integrated with the capture device 202 as described in more detail below to remove irrigated particulates.

As illustrated in FIG. 8C, after the patient's heart has been irrigated and particulates removed, the irrigation device 360 may be removed or withdrawn from the heart. In some embodiments, the irrigation conduits 364 are moved to the stored positions within the delivery tube 362 (e.g., by moving the pusher shaft 373 proximally) and the delivery tube 362 is removed from the patient through the cored opening. The heart pump or inflow cannula may then be implanted or attached as described above. In other embodiments, the delivery tube 362 may be removed or withdrawn from the heart through the cored opening without moving the irrigation conduits 364 to the stored positions prior to installing the heart pump or inflow cannula.

In some embodiments, the irrigation device 360 as described herein may be integrated with the surgical coring tool 350. As described above with respect to the coring tool 250, a body or shaft of the surgical coring tool 350 may include a lumen 351. The delivery tube 362 or capture device 202 (e.g., irrigation conduits 364) may be configured to extend through such a lumen to be deployed into the patient's heart (e.g., after coring by the surgical coring tool 350). In some embodiments, the lumen of the coring tool 350 may serve as a housing or delivery tube the irrigation conduits 364 may be stowed in the stored positions without the delivery tube 362. In the deployed positions, the irrigation conduits 364 may extend out of sidewall openings in the shaft of the coring tool 350. In other embodiments, the delivery tube 362 may extend through the lumen of the coring tool 350 with the irrigation conduits stowed within.

Figure 9:
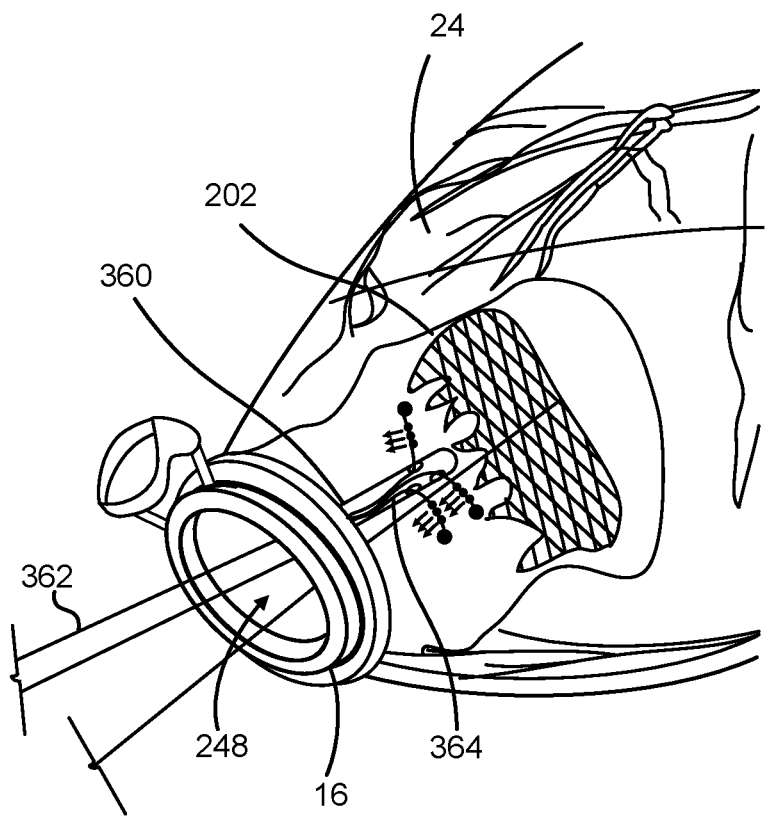
FIG. 9 is an illustration of an example medical system including both a removable particulate capture device and a tissue irrigation device in accordance with aspects of the invention.

FIG. 9 illustrates an embodiment of a medical system 400 including both the capture device 202 and irrigation device 360 as described above. The irrigation device 360 may be configured to be deployed or work in conjunction with the capture device 202. For example, as described above, the capture device 202 may be inserted into the patient's heart and capture particulates released by the coring procedure and that are irrigated by the tissue irrigating device 360. In such embodiments, the capture device 202 may be inserted and deployed within the patient's heart prior to a coring procedure. The irrigation device 360 may then be delivered and deployed through the cored opening after the coring procedure to irrigate the cored opening or heart. In other embodiments, the irrigation device 360 may be integrated with the capture device 202. For example, the capture device 202 and tissue irrigating device 360 may share an outer sheath or delivery tube (e.g., delivery tube 362, outer sheath 242). In such embodiments, the capture device 202 and tissue irrigating device 360 may be delivered in their stored or collapsed configurations into the heart via the shared delivery tube (e.g., prior to a coring procedure). The irrigation conduits 364 and the expandable basket 204 may then be moved to the deployed or expanded configurations when positioned in the heart. In some embodiments, the devices 202, 360 may additionally share a pusher or delivery shaft (e.g., pusher shaft 373, delivery shaft 234) coupled to the irrigation conduits 364 and expandable basket 204. In yet other embodiments, both the capture device 202 and irrigation device 360 may be integrated with a surgical coring tool (e.g., surgical coring tools 250, 350). For example, the lumen of the surgical coring tool may serve as an outer sheath or delivery tube. In other embodiments, the capture device 202 and irrigation device 360 may be configured to extend through the lumen of the coring tool.

Figure 10A:
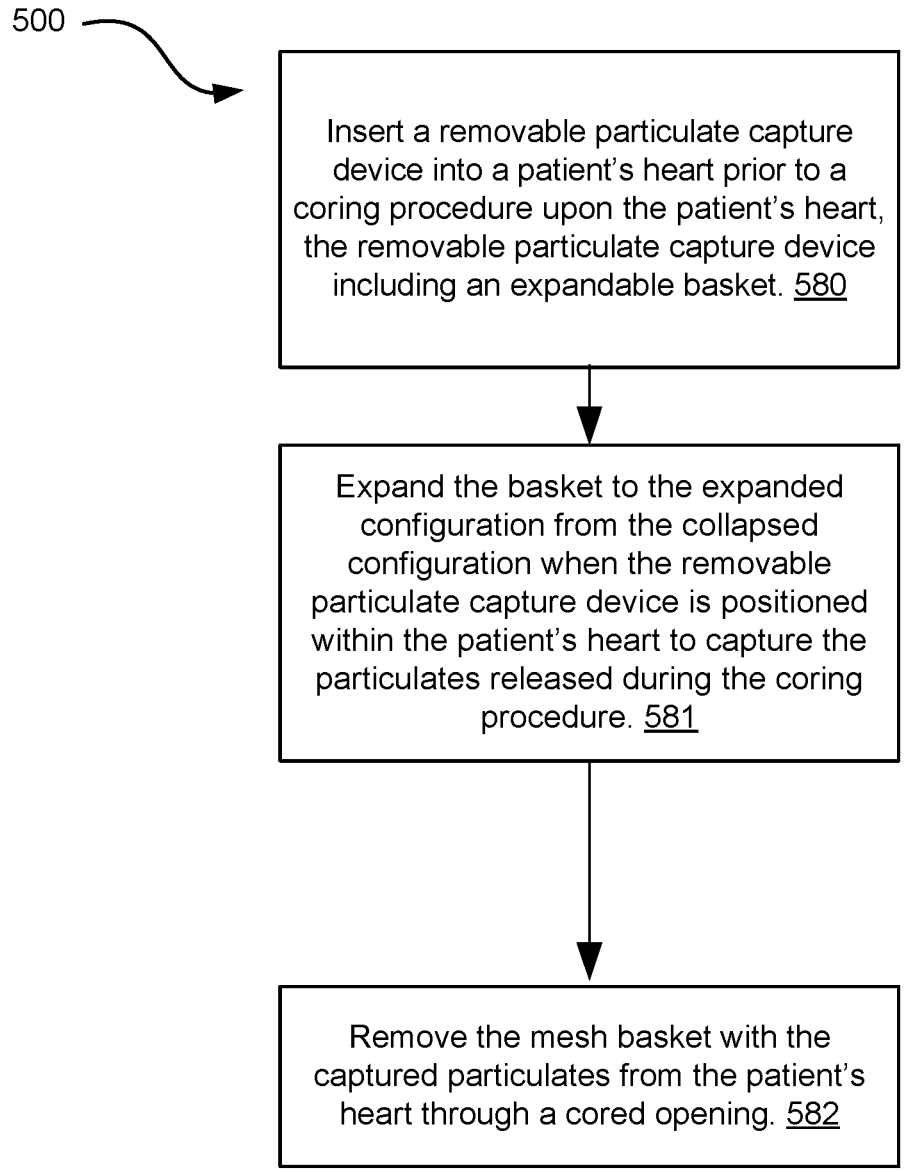
FIGS. 10A-10C are a series of flowcharts illustrating exemplary methods in accordance with aspects of the invention.
Figure 10B:
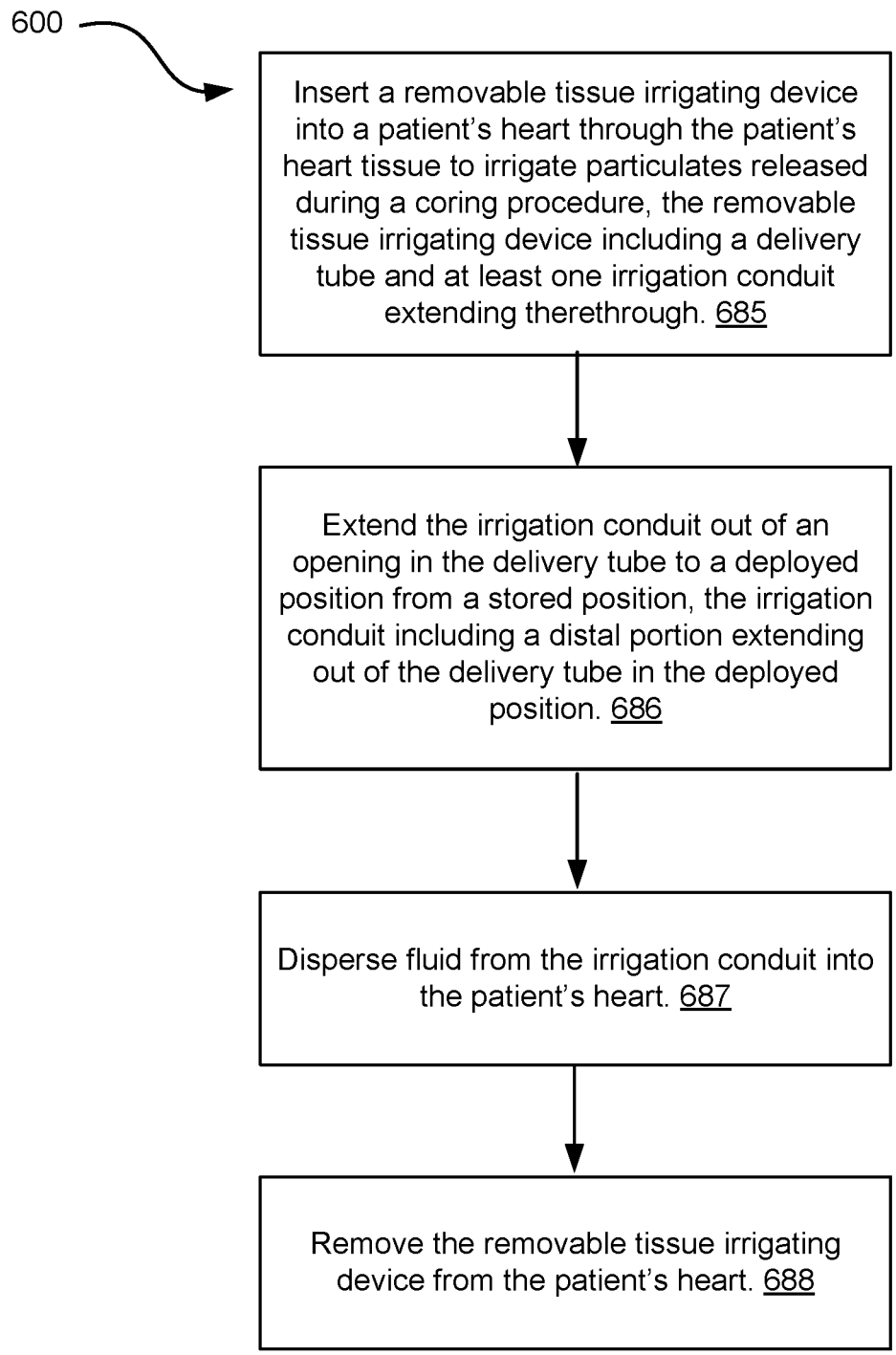
Figure 10C:
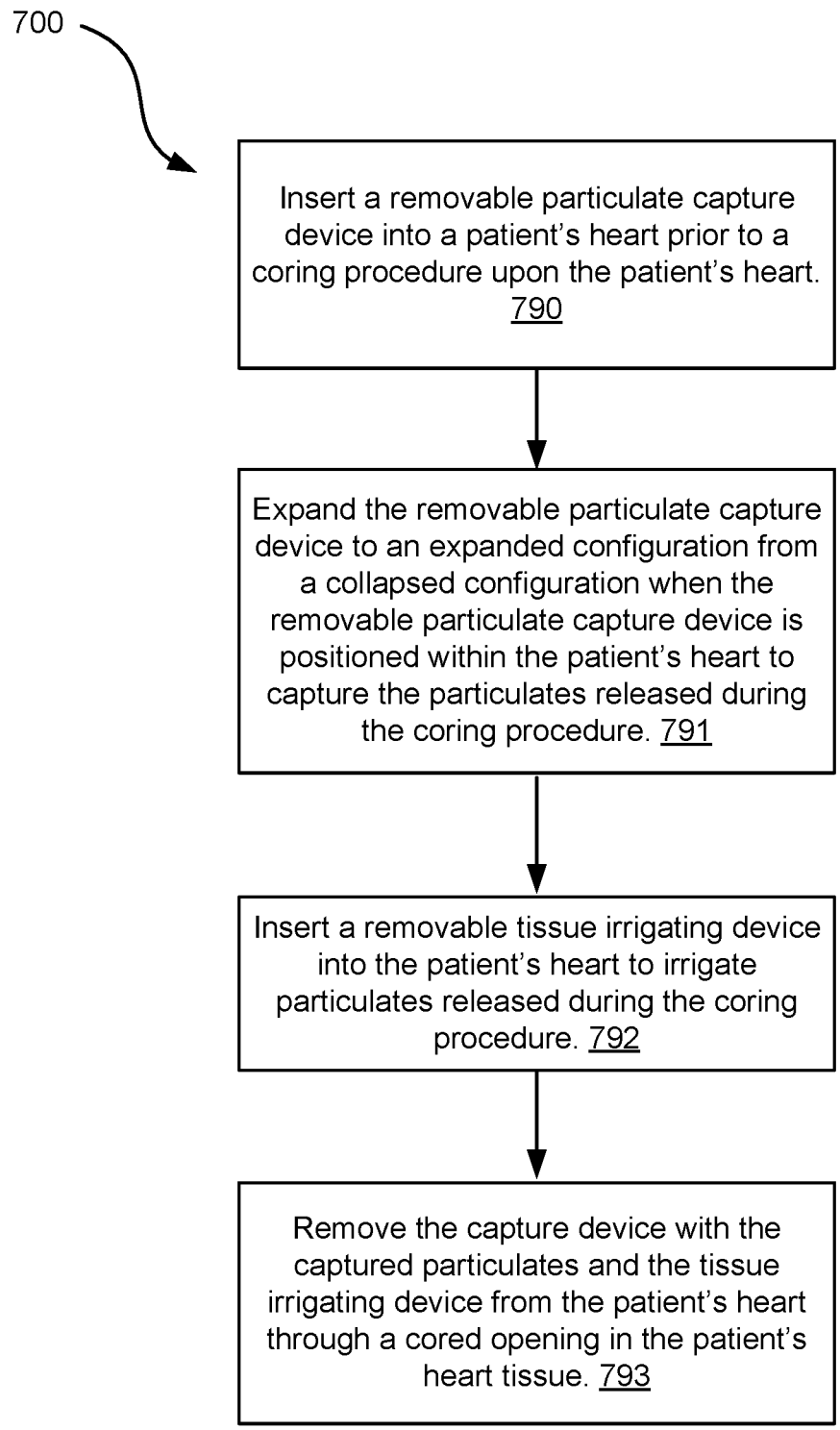

FIGS. 10A-10C are a series of flowcharts illustrating exemplary methods 500, 600, and 700 for capturing and removing particulates, irrigating particulates, and irrigating, capturing, and removing particulates, respectively, with any of the systems and devices as described herein during heart pump implantation. One or more of any steps of methods 500-700 as described herein may be included, combined, or substituted within any of the other methods. Further, steps may be removed, re-ordered, substituted, or added.

With reference to FIG. 10A, exemplary method 500 for capturing particulates during heart pump implantation may include inserting a removable particulate capture device (e.g., capture device 202) as described herein into a patient's heart prior to a coring procedure upon the patient's heart 580. For example, the method may include inserting a delivery or guide tube or catheter housing the expandable basket in a collapsed configuration into the patient's heart.

The removable particulate capture device includes an expandable basket (e.g., expandable basket 204) movable between collapsed and expanded configurations. The method 500 further includes expanding the expandable basket to the expanded configuration from the collapsed configuration when the removable particulate capture device is positioned within the patient's heart to capture the particulates released during the coring procedure 581. For example, the expandable basket may include self-expanding structural frame members or the method may include inflating a balloon or moving an actuator to expand the expandable basket. The method 500 may include expanding the expandable basket until it contacts walls of a ventricle (e.g., the left ventricle). The method 500 includes removing the expandable basket with the captured particulates from the patient's heart through a cored opening 582.

In some embodiments, the method 500 may include collapsing the expandable basket to the collapsed configuration from the expanded configuration after the coring procedure and prior to removing the expandable basket from the patient's heart. In some embodiments, the method 500 includes collapsing the expandable basket to the collapsed configuration from the expanded configuration prior to inserting the removable particulate capture device into the patient's heart. The method 500 may include creating an access site through a surface of the patient's heart that the removable particulate capture device can be inserted through into the patient's heart. The method 500 may include coring a portion of the patient's heart after inserting the removable particulate capture device within the patient's heart. The method 500 may include inserting a removable tissue irrigating device (e.g., irrigating device 360) into the patient's heart configured to irrigate particulates released during the coring procedure after coring the portion of the patient's heart. In further embodiments, the method 500 may include attaching a ventricular cuff or inflow cannula of a VAD to the heart.

With reference to FIG. 10B, exemplary method 600 for irrigating particulates during heart pump implantation may include inserting a removable tissue irrigating device (e.g., irrigating device 360) into a patient's heart (e.g., a left ventricle) through the patient's heart tissue to irrigate particulates released during a coring procedure 685. The removable tissue irrigating device includes a delivery tube and at least one irrigation conduit extending therethrough. The method 600 includes extending the irrigation conduit out of an opening in the delivery tube to a deployed position from a stored position 686. The irrigation conduit is substantially positioned within the delivery tube in the stored position. The irrigation conduit includes a distal portion extending out of the delivery tube in the deployed position. The method 600 includes dispersing fluid from the irrigation conduit into the patient's heart 687. The method 600 further includes removing the removable tissue irrigating device from the patient's heart 688 (e.g., prior to, after, or concurrently with removing the released particulates). The method may include removing the particulates released by the coring procedure or disperse fluid as described herein. The method 600 may include coring a portion of the patient's heart tissue prior to inserting the removable tissue irrigating device into the patient's heart. The method 600 may include inserting the removable tissue irrigating device into the patient's heart through a cored opening in the patient's heart tissue.

In some embodiments, the method 600 includes inserting a removable particulate capture device (e.g., capture device 202) into the patient's heart configured to capture and remove irrigated or released particulates. The removable particulate capture device may be inserted prior to a coring procedure. In some embodiments, the method 600 includes temporarily switching a cardiopulmonary bypass machine coupled to the patient's heart from an on position to an off position to pump irrigated or released particulates out of the heart. In some embodiments, an aspiration catheter is used to suction out the particulates. In some embodiments, a clinician may remove the particulates with tweezer or other suitable tools.

With reference to FIG. 10C, exemplary method 700 for irrigating, capturing, and removing particulates during heart pump implantation may include inserting a removable particulate capture device (e.g., capture device 202) as described herein into a patient's heart prior to a coring procedure upon the patient's heart 790. The method 700 includes expanding the removable particulate capture device to an expanded configuration from a collapsed configuration when the removable particulate capture device is positioned within the patient's heart to capture the particulates released during the coring procedure 791. The method includes inserting a removable tissue irrigating device (e.g., irrigating device 360) into the patient's heart to irrigate particulates released during the coring procedure 792. The method 700 includes removing the capture device with the captured particulates and the tissue irrigating device from the patient's heart through a cored opening in the patient's heart tissue 793.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The terms "connected" or "attached" are to be construed as partly or wholly contained within, coupled to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for capturing particulates during heart pump implantation, the method comprising:
   attaching a ventricular cuff to a patient's heart;
   with the ventricular cuff attached to the patient's heart, inserting a removable particulate capture device through the ventricular cuff into a ventricle of the patient's heart prior to a coring procedure upon the patient's heart, the removable particulate capture device comprising an expandable basket movable between collapsed and expanded configurations;
   expanding the expandable basket within the ventricle to the expanded configuration from the collapsed configuration;
   conducting the coring procedure;
   capturing, within the ventricle, particulates released during and/or after the coring procedure within the expandable basket; and
   removing the expandable basket with the captured particulates from the ventricle.

2. The method of claim 1, further comprising collapsing the expandable basket to the collapsed configuration from the expanded configuration within the ventricle prior to removing the expandable basket from the ventricle.

3. The method of claim 1, further comprising attaching an inflow cannula of a heart pump to the patient's heart after removing the expandable basket from the ventricle.

4. The method of claim 1, wherein expanding the expandable basket to the expanded configuration comprises expanding the expandable basket until the expandable basket contacts inner walls of the ventricle.

5. The method of claim 1, further comprising collapsing the expandable basket to the collapsed configuration from the expanded configuration prior to inserting the removable particulate capture device within the patient's heart.

6. The method of claim 1, wherein conducting the coring procedure comprises coring a portion of the patient's heart with a surgical coring tool having a lumen through which the removable particulate capture device extends into the ventricle during the coring of the portion of the patient's heart.

7. The method of claim 1, further comprising creating an access site through a surface of the patient's heart that the removable particulate capture device is inserted through into the ventricle.

8. The method of claim 7, wherein the access site is different than a second access site for the coring procedure.

9. The method of claim 1, wherein the expandable basket comprises a mesh basket.

10. The method of claim 1, wherein the expandable basket comprises self-expandable structural frame members.

11. The method of claim 1, wherein expanding the expandable basket to the expanded configuration comprises inflating a balloon to expand the expandable basket.

12. The method of claim 1, wherein expanding the expandable basket to the expanded configuration comprises axially moving a hub relative to a delivery shaft, the hub being coupled to structural frame members of the expandable basket and the delivery shaft.

13. The method of claim 1, wherein inserting the removable particulate capture device into the ventricle comprises inserting a delivery catheter into the ventricle.

14. The method of claim 13, wherein the delivery catheter is configured to surround at least a portion of the removable particulate capture device.

15. The method of claim 1, further comprising inserting a removable tissue irrigating device through the ventricular cuff into the ventricle, wherein the removable tissue irrigating device is configured to irrigate particulates released into the ventricle during and/or after the coring procedure.

* * * * *